United States Patent
Foster et al.

(10) Patent No.: US 7,615,560 B2
(45) Date of Patent: Nov. 10, 2009

(54) THIENOPYRIMIDINES AS COOLING AGENTS

(75) Inventors: Alison Jayne Foster, Wirral (GB); Cornelis Paul Erik van der Logt, Vlaardingen (NL); Afrodite Lourbakos, Vlaardingen (NL); Erwin Werner Tareilus, Vlaardingen (NL)

(73) Assignee: Conopco, Inc., Englewood Cliffs, NJ (US)

( * ) Notice: Subject to any disclaimer, the term of this patent is extended or adjusted under 35 U.S.C. 154(b) by 126 days.

(21) Appl. No.: 11/791,268

(22) PCT Filed: Nov. 7, 2005

(86) PCT No.: PCT/EP2005/011972
§ 371 (c)(1),
(2), (4) Date: Oct. 11, 2007

(87) PCT Pub. No.: WO2006/058600
PCT Pub. Date: Jun. 8, 2006

(65) Prior Publication Data
US 2008/0170999 A1  Jul. 17, 2008

(30) Foreign Application Priority Data
Nov. 30, 2004 (GB) ................... 0426266.3

(51) Int. Cl.
*A61K 31/505* (2006.01)
*C07D 471/04* (2006.01)
*C07D 471/22* (2006.01)

(52) U.S. Cl. ..................................... 514/267

(58) Field of Classification Search ................ 514/257, 514/267; 544/247, 250
See application file for complete search history.

(56) References Cited

U.S. PATENT DOCUMENTS
2004/0018954 A1   1/2004   Su et al.

FOREIGN PATENT DOCUMENTS
EP   0 452 002 A2   10/1991
GB   1 354 733   5/1974
WO   2004/072074 A1   8/2004

OTHER PUBLICATIONS

Potacek, et al., Reactions of 2-ethoxymethyleneamino-3-cyano-4,5,6,7-tetrahydrobenzo[b]thophene with Nitrogen Nucleophiles, Czech. Chem. Papers, 46(1), 34-37 (1992).*
International Search Report Application No. PCT/EP 2005/011972 mailed Feb. 27, 2006.
Search Report Application No. GB 0426266.3 under Section 17 dated Apr. 8, 2005.
Abstract XP002365034 Beilstein Institut Zur Forderung der Chemischen Wissenschaften and Z.A. Hozien et al.: "Synthesis of some biologically active agents derived from thieno'2,3-dpyrimidine derivatives" vol. 52, No. 10, 1997, pp. 753-758.
R. Anderskewitz et al.: Pyrrolidinohydroquinazolines—Bioorg. Med. Chem. Lett., vol. 15, No. 3, pp. 669-673, XP002364991.
Potecek et al. Chemica Scripta (1988), 35 (Chem. Heterocycl. Compd.), ISSN 0165-3253, pp. 484-486, especially abstract.
Morgensen et al., Chemica Scripta (1988), 28(2), ISSN 0004-2056, pp. 195-200, especially abstract.

* cited by examiner

*Primary Examiner*—James O Wilson
*Assistant Examiner*—Erich A Leeser
(74) *Attorney, Agent, or Firm*—Michael P. Aronson

(57) ABSTRACT

Use of a compound of formula (I) where $R^1$ is a $C_{4-6}$ alkylene linkage optionally substituted by a $C_{1-4}$ alkyl group; $R^2$ is =NH, —$NH_2$ or —OH; $R^3$ is $C_{1-5}$ alkyl optionally terminated by a hydroxy, phenyl or a 5- or 6-membered heterocyclic group such as furyl or N-imidazolyl and $R^4$ is H; or $R^3$ and $R^4$ together form a $C_{3-5}$ alkylene linkage; to produce a topical refreshing or cooling sensation in a mammal such as a human.

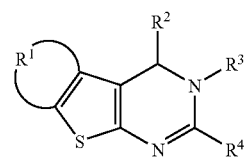

(I)

9 Claims, No Drawings

THIENOPYRIMIDINES AS COOLING AGENTS

FILED OF THE INVENTION

The invention relates to tricyclic compounds which are capable of producing a refreshing or cooling sensation when they are brought into contact with the human body. Such compounds have applications in many fields, particularly in oral and personal hygiene products and foodstuffs.

BACKGROUND OF THE INVENTION

A known compound for producing an oral sensation of cold is menthol (2-isopropyl-5-methyl-cyclohexanol), which has been extensively applied as an additive in, for example, foodstuffs and oral hygiene products. It is used primarily because it elicits a sensation of coolness in the mouth, and because it has a pleasing mint flavour and odour. The cooling effect of menthol is due to the action of menthol on the nerve endings of the human body which detect hot and cold stimuli. In particular, menthol is believed to activate cold receptors on nerve endings. However, the use of menthol is limited by its strong minty smell and relative volatility.

To find alternative cooling compounds, many investigations have focused upon compounds which are menthol derivatives or analogues. Other cooling compounds have been based upon fundamentally different molecular species. A particularly well researched group of compounds comprises 1,4-disubstituted tetrahydropyrimidinone derivatives.

We have now found a class of tricyclic molecules which are substituted hydrobenzothienopyrimidines or analogues thereof and which have excellent cooling or refreshing properties.

DEFINITION OF THE INVENTION

According to a first aspect of the invention, there is provided the use of a compound of formula (I)

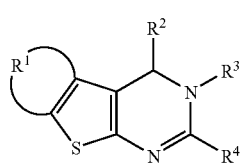

where $R^1$ is a $C_{4-6}$ alkylene linkage optionally substituted by a $C_{1-4}$ alkyl group;

$R^2$ is =NH, —NH$_2$ or —OH;

$R^3$ is $C_{1-5}$ alkyl optionally terminated by a hydroxy, phenyl or a 5- or 6-membered heterocyclic group such as furyl or N-imidazolyl and $R^4$ is H; or $R^3$ and $R^4$ together form a $C_{3-5}$ alkylene linkage;

to produce a topical refreshing or cooling sensation in a mammal such as a human.

According to a second aspect of the invention, there is provided a compound of formula (II):

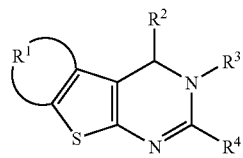

where $R^1$ is a $C_{4-6}$ alkylene linkage optionally substituted by a $C_{1-4}$ alkyl group;

$R^2$ is =NH, —NH$_2$ or —OH;

$R^3$ is $C_{1-5}$ alkyl optionally terminated by a hydroxy, phenyl or a 5- or 6-membered heterocyclic group such as furyl or N-imidazolyl and $R^4$ is H; or $R^3$ and $R^4$ together form a $C_{3-5}$ alkylene linkage;

with the proviso that when $R^1$ is an unsubstituted $C_4$ or $C_5$ akylene linkage and
  $R^2$ is —NH$_2$,
  then when $R^4$ is hydrogen, $R^3$ is other than an unsubstituted $C_{1-5}$ alkyl group
  or $R^3$ and $R^4$ do not together form a $C_{3-5}$ alkylene linkage;

when $R^1$ is an unsubstituted $C_4$ or $C_5$ alkylene linkage and $R^2$ is =NH,
  then when $R^4$ is hydrogen, $R^3$ is other than —(CH$_2$)$_2$—CH$_3$,
    —CH$_2$—CH—(CH$_3$)$_2$, —(CH$_2$)$_3$—CH$_3$, —(CH$_2$)$_2$—OH, —CH$_2$-Fy or —(CH$_2$)$_3$-Nlm
  or $R^3$ and $R^4$ do not together form a $C_3$ or a $C_5$ alkylene linkage;

when $R^1$ is an unsubstituted $C_4$ alkylene linkage, $R^2$ is =NH and $R^4$ is hydrogen,
  then $R^3$ is other than —CH$_2$-Ph; and when $R^1$ is an unsubstituted $C_5$ alkylene linkage, $R^2$ is =NH and $R^4$ is hydrogen,
  then $R^3$ is other than —(CH$_2$)$_3$—OH.

Also believed to be novel and which may be claimed per se is any compound of formula (I) as hereinbefore defined, wherein $R^2$ is —OH.

A third aspect of the invention provides a composition comprising at least one compound of formula (I) as hereinbefore defined and at least one other ingredient, for producing a topical refreshing or cooling sensation in a mammal such as human.

A fourth aspect of the present invention provides a method of imparting a topical refreshing or cooling sensation to a mammal such as human comprising applying topically to said human, at least one compound of formula (I) as hereinbefore defined.

DETAILED DESCRIPTION OF THE INVENTION

Unless otherwise specified in the following description, alkyl represents a linear or cyclic saturated hydrocarbon which may be straight-chain or branched, and preferably contains up to 20 carbon atoms. Similarly, alkenyl represents a linear or cyclic, straight-chain or branched unsaturated hydrocarbon which preferably contains up to 20 carbon atoms. When an alkyl group is linear, it preferably contains from 1 to 10, more preferably from 1 to 6 carbon atoms.

Suitable examples include methyl, ethyl, propyl, butyl, pentyl and hexyl, and isomers thereof. For example, a $C_4$ group can be present in the form of n-butyl, iso-butyl, sec-butyl or tert-butyl. When an alkyl group is cyclic, it preferably contains from 5 to 10 carbon atoms, and may be, for example, cyclopentyl, cyclohexyl, cycloheptyl, decalin or adamantyl.

For the avoidance of doubt, the following abbreviations are used in this specification:

-Ph phenyl
-Fy furyl
-NIm N-imidazolyl

A subset of particularly preferred compounds of formula (I) are those wherein $R^1$ is a $C_4$ or $C_5$ alkylene linkage, preferably unsubstituted; $R^2$ is =NH, $R^3$ is a $C_2$ or $C_3$ straight chain alkyl group optionally terminated by a hydroxyl, phenyl, furyl or N-imidazolyl group, a $C_3$ or $C_4$ branched alkyl group and $R^4$ is hydrogen; or $R^3$ and $R^4$ together form a $C_{3-5}$ alkylene linkage.

The compounds of formula (I) and compositions contain them produce a refreshing or cooling sensation upon topical application to the skin and/or mucosal membrane of a human or other mammalian body. A "refreshing or cooling sensation" as used throughout is thus intended to mean any sensation of freshness and/or coolness which is perceived by human or animal body. Such a sensation is analogous to the sensation produced by compounds such as menthol, and/or the sensation elicited when cold-sensitive receptors, such as those identified in McKemy et al, Nature, Vol. 416, 2002, 52-58, are stimulated.

Compositions and Uses

A refreshing or cooling sensation is desirable in many different applications. For example, the compounds and compositions of the invention have applications in a number of personal hygiene, oral hygiene and food product compositions. Personal hygiene applications include lotions, shaving cream, post shaving preparations, shampoos, hair conditioners, facial cleansers, soaps, bath oils and foams, antiperspirants, deodorants. Oral hygiene applications include toothpastes, mouthwashes, dental floss, chewing gum and breath fresheners. Foodstuff applications include beverages, spreads, ice-creams and confectionery. Possible other applications where a cooling sensation may be desirable include pharmaceutical products for oral conditions (for example chewable pharmaceutical products, oral creams, gels or ointments or throat lozenges), pharmaceutical products for application to the skin (for example skin creams, ointments or lotions, especially any for alleviation or treatment of itch, inflammation or other irritation or dry skin), tobacco products, insect repellents and cosmetics.

The compounds may be used alone, or in a composition in combination with another substance or substances such as a carrier. The nature of these additional substances, and the relative proportions of components of the composition will depend on a number of factors, such as the specific use for which the composition is employed. The compositions may be used in a variety of applications, such as those discussed above. Particularly preferred uses include personal hygiene products such as deodorant, shower gel and skin cream; oral hygiene products such as toothpastes and mouthwashes; and foodstuffs, such as beverages, ice-creams, confectionery and spreads.

Compounds of formula (I) and compositions containing them may also be used, for example, in applications such as personal hygiene products such as deodorant, shower gel and skin cream; oral hygiene products such as mouthwash and toothpaste; and food products. The compounds may have particularly useful applications in foodstuffs such as beverages, spreads, confectionery and ice-cream.

Such applications may include the fields of personal hygiene products (including lotions, shaving cream, post shaving preparations, shampoos, conditioners, facial cleansers, soaps, bath oils and foams, antiperspirants and deodorants); oral hygiene products (including toothpastes, mouthwashes, dental floss, chewing gum and breath fresheners); food products (including beverages, spreads, ice-creams and confectionery); and other applications where a cooling sensation may be desirable (including pharmaceutical products such as chewable pharmaceutical products or throat lozenges, tobacco products, insect repellents and cosmetics).

Particularly preferred are compositions for use as toothpastes, mouthwashes and food products such as confectionery, beverages, spreads and ice-cream. The specific nature of the composition (e.g. the nature of the additional components, the relative proportions of the components and the physical nature of the composition) will depend on the particular application.

The compound or compounds of formula (I) are preferably included in any composition in an amount of from 0.00001% to 3%, eg from 0.001% to 3% by weight, based on the total weight of the composition. An especially preferred range is from 0.0001% to 0.3% by weight. The compound may present in an amount of from 0.0003% to 0.1% or from 0.003% to 0.1%.

Preparation of Compounds

Many compounds of formulae (I) and (II) disclosed above are commercially available but those which are not may be made according to a general process shown in Scheme 1:

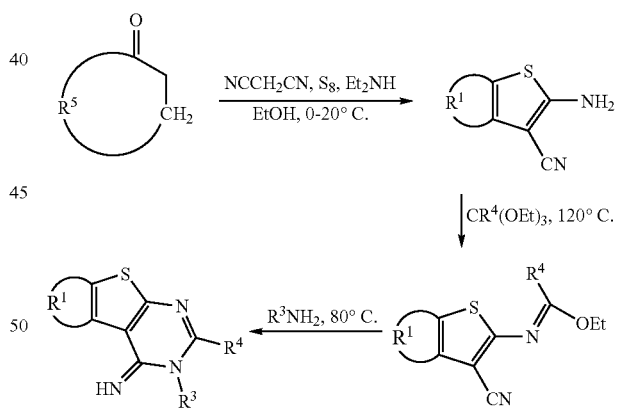

wherein $R^1$, $R^3$ and $R^4$ have the same meanings as in formula (I); $R^5$ is a group as defined for $R^1$ in formula 1 but minus one carbon atom in the alkylene linkage and =NH represents the group $R^2$ or when $R^2$ represents —$NH_2$, the =NH group may be converted to this primary amino group by reduction with an appropriate reducing agent such as lithium aluminium hydride or soldium borohydride, or when $R^2$ in the final product represents —OH then the =NH group may be converted to =O in the presence of alkali or acid followed by reduction to —OH by any conventional technique such as for reduction of =NH to $NH_2$.

Scheme 1

In scheme 1, the temperatures shown are exemplary and scheme 1 is not limited to use of these temperatures.

Compounds of formula (I) or formula (II) may also be prepared by methods as, or analogous to, those described in Chowdhury A. Z. M. S., J. Bangladesh Acad. Sci., 1999, 23, 59-67, in Hozein, Z. A. et al, Pharmazie, 1997, 52 (10), 753-758, or in Potacek et al, Studies in Organic Chemistry (Amsterdam) (1989) 35, (Chem. Heterocycl. Compd.), 484-6.

Preferred embodiments of the invention will now be described by way of example only. Further modification within the scope of the present invention will be apparent to the person skilled in the art.

EXAMPLES

Example 1

Preparation of 3-propyl-5,6,7,8-tetrahydro-3H-benzo [4,5]-thieno[2,3-d]pyrimidin-4-ylidene amine To cyclohexanone (100 mmol), malononitrile (100 mmol), sulfur (100 mmol) in ethanol (30 ml) was added morpholine (100 mmol) slowly at 0° C. The resulting mixture was stirred at room temperature for 4 hours. After standing overnight it was diluted with water and the solid was collected and recrystallised from ethanol.

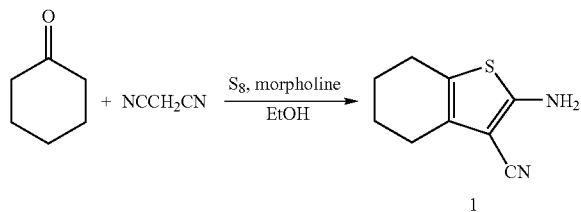

A mixture of 1 (10 mmol) and triethyl orthoformate (10 ml) was heated for 3 hours at 120° C. The reaction mixture was allowed to cool to room temperature, water (50 ml) was added and the resulting solid was collected by filtration and purified by column chromatography (silica, petroleum ether:ethyl acetate 20:1).

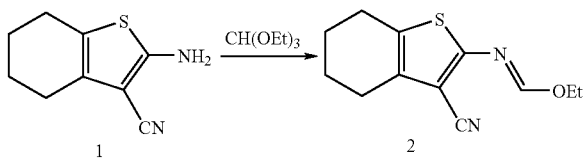

A mixture of 2 (3.36 mmol) and n-butylamine (101 mmol) was stirred at 80° C. for 3 hours. Excess amine was removed in vacuo and the residue was triturated with ice/water and then filtered. The solid was purified by column chromatography (dichloromethane:methanol 30:1).

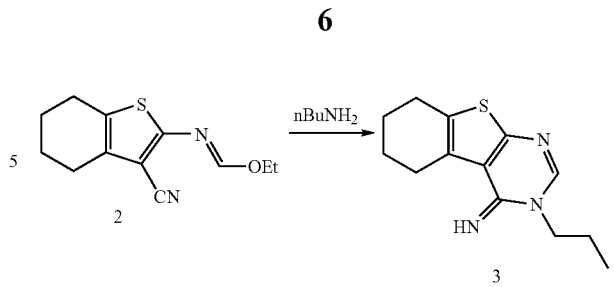

Assay

Humans can detect changes in temperature from noxious cold (<8 C) to noxious heat (>52 C) due to activation of sensory nerve fibers. "The principal temperature sensors in the sensory nerve fibers are members of a family of transient receptor potential (TRP) cation channels" (Voets et al., 2004). In humans the sensation of cooling is elicited by activation of channel TRPM8, which is activated at temperatures below 28 C (Voets et al., 2004). Furthermore human TRPM8 is activated by compounds such as menthol (Brauchi et al., Proc. Natl. Acad. Sci. USA, 2004, Oct. 26; 101 (43):15494-9; Voets et al., Nature, 2004, 430 (7001): 748-54). A heterologous expression system, in which HEK cells stably expressing the human TRPM8 channel, was used to set up a screening system in order to search for compounds that elicit a cooling sensation.

The open reading frame of human cDNA TRPM8 from position 41-3355bp was amplified from a human prostate cDNA library (Stratagene) using primers TATAGT-TAACGCCGCCACCATGTC-CTTTCGGGCAGCCAGGCTCAG and TATATCTAGAT-TATTTGATTTTATTAGCAATCTCTTTC as previously described previously (Tsavalier et al., 2001).

HEK 293 cells were transfected with human TRPM8 cDNA that was cloned into a pcDNA4 vector, using a standard calcium phosphate method (Wigler et al., 1977). The transfected cells were placed under selective pressure by growth in 100 μg/mL zeocin (Invitrogen) and cells stably expressing the human TRPM8 were generated.

Cells stably expressing the human TRPM8 were seeded in a 96 well plate (coated with polylysine) at a density of $10^5$ cells /well in 200 μl of media. The next day the cell medium was removed and the cells were incubated a DMEM solution (supplemented with 0.001% BSA w/w, 0.01% FCS v/v, 0.02% plurinoc acid, 1 mM probenicide) that contained the calcium sensitive fluorescent dye fluo-4 (~3 μM, Molecular Probes) at 37° C. for 1 hr. The dye was then removed and the cells were incubated in a Tyrodes buffer (containing 1 mM probenicide, pH 7.4) pre-equilibrated at a certain temperature (i.e 37° C.) and the intracellular calcium levels were monitored at the same temperature, using the Novostar plate reader. The cells in each well were illuminated at 480 nm, and the fluorescent light emitted at 510 nm was measured. The fluorescence was determined before (basal fluorescence) and after the addition of increasing concentrations of a test compound. The maximal increase in fluorescence (DFmax) caused by a compound, was measured as the peak fluorescence induced by that compound minus the basal fluorescence. The potency of a compound is expressed as the $EC_{50}$ and it is the concentration of the compound that produces one-half of the maximal response (DFmax).

In the above assay, the compound of Example 1 was found to have an $EC_{50}$ of 6.5 μM. The following example compounds were either sourced commercially or made by the route of Reaction Scheme 1 and were found to have the $EC_{50}$ values quoted.

Examples 2-12

The following example compounds were tested for activity in the above assay.

| | | Compound | | | |
|---|---|---|---|---|---|
| Ex | $R^1$ | $R^2$ | $R^3$ | $R^4$ | $EC_{50}$ (μM) |
| 2 | —$(CH_2)_4$— | =NH | —$(CH_2)_5$— | with $R^3$ | 9 |
| 3 | —$(CH_2)_4$— | =NH | —$(CH_2)_2$—OH | H | 55 |
| 4 | —$(CH_2)_4$— | =NH | —$(CH_3)_3$—OH | H | 100 |
| 5 | —$(CH_2)_4$— | =NH | —$(CH_2)_3$-NIm | H | 85 |
| 6 | —$(CH_2)_5$— | =NH | —$(CH_2)_3$—$CH_3$ | H | 25 |
| 7 | —$(CH_2)_4$— | =NH | —$CH_2$-Fy | H | 15 |
| 8 | —$(CH_2)_4$— | =NH | —$(CH_2)_3$— | with $R^3$ | 55 |
| 9 | —$(CH_2)_4$— | =NH | —$CH_2$—Ph | H | 30 |
| 10 | —$(CH_2)_5$— | =NH | —$CH_2$—CH—$(CH_3)_2$ | H | 70 |
| 11 | —$(CH_2)_4$— | =NH | —$(CH_2)_2$—OH | H | 20 |
| 12 | —$(CH_2)_4$— | —$NH_2$ | —$(CH_2)_5$— | with $R^3$ | 10 |

The invention claimed is:

1. A composition comprising at least one compound of formula (I):

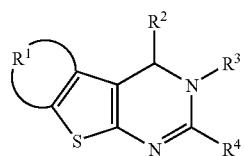

(I)

where $R^1$ is a $C_{4-6}$ alkylene linkage optionally substituted by a $C_{1-4}$ alkyl group;
$R^2$ is =NH or —$NH_2$;
$R^3$ is $C_{2-5}$ alkyl optionally terminated by a hydroxyl, phenyl or a 5- or 6-membered heterocyclic group such as furyl or N-imidazolyl and $R^4$ is H; or
$R^3$ and $R^4$ together form a $C_{3-5}$ alkylene linkage;
to produce a topical refreshing or cooling sensation in a mammal such as a human; and
at least one other ingredient.

2. A composition according to claim 1, wherein in formula (I) $R^1$ is a $C_4$ or $C_5$ alkylene linkage, preferably unsubstituted; $R^2$ is =NH, $R^3$ is a $C_2$ or $C_3$ straight chain alkyl group optionally terminated by a hydroxyl, phenyl, furyl or N-imidazolyl group or is a $C_3$ or $C_4$ branched alkyl group and $R^4$ is hydrogen; or $R^3$ and $R^4$ together form a $C_{3-5}$ alkylene linkage.

3. A composition according to claim 1, in the form of a personal hygiene product, an oral hygiene product, a skin product or a food.

4. A personal hygiene product composition according to claim 1, formulated as a lotion, shaving cream, post shaving preparation, shampoo, hair conditioner, facial cleanser, soap, bath oil, bath form, anti-perspirant or deodorant.

5. An oral hygiene product composition according to claim 1, formulated as a toothpaste, mouthwash, dental floss, chewing gum or breath freshener.

6. A skin product composition according to claim 1, formulated as a skin cream, skin ointment or skin lotion.

7. An oral pharmaceutical product composition according to claim 1, formulated as an oral gel, oral cream, oral ointment or throat lozenge.

8. A food composition according to claim 1, formulated as a beverage, spread, ice cream or a confection.

9. A composition according to claim 1, comprising from 0.00001% to 3% by weight of the total composition of the compound or compounds of formula (I).

* * * * *